//(12) United States Patent
Li et al.

(10) Patent No.: US 6,991,789 B2
(45) Date of Patent: Jan. 31, 2006

(54) METHODS OF MODULATING INTRACELLULAR DEGRADATION RATES OF TOXINS

(75) Inventors: Shengwen Li, Irvine, CA (US); Kei Roger Aoki, Irvine, CA (US)

(73) Assignee: Allergas, Inc., Irvine, CA (US)

( * ) Notice: Subject to any disclaimer, the term of this patent is extended or adjusted under 35 U.S.C. 154(b) by 0 days.

(21) Appl. No.: 10/880,192

(22) Filed: Jun. 29, 2004

(65) Prior Publication Data

US 2005/0287175 A1   Dec. 29, 2005

(51) Int. Cl.
A61K 38/48   (2006.01)

(52) U.S. Cl. .................................................. 424/94.63
(58) Field of Classification Search ................ 530/350; 424/190.1, 184.1, 94.63
See application file for complete search history.

(56) References Cited

U.S. PATENT DOCUMENTS

| | | |
|---|---|---|
| 5,437,291 A | 8/1995 | Pasricha et al. |
| 5,670,484 A | 9/1997 | Binder |
| 5,714,468 A | 2/1998 | Binder |
| 5,766,605 A | 6/1998 | Sanders et al. |
| 5,989,545 A | 11/1999 | Foster et al. |
| 6,063,768 A | 5/2000 | First |
| 6,139,845 A | 10/2000 | Donovan |
| 6,299,893 B1 | 10/2001 | Schwartz et al. |
| 6,306,423 B1 | 10/2001 | Donovan et al. |
| 6,312,708 B1 | 11/2001 | Donovan |
| 6,358,917 B1 | 3/2002 | Carruthers et al. |
| 6,423,319 B1 | 7/2002 | Brooks et al. |
| 6,447,787 B1 | 9/2002 | Gassner et al. |
| 6,458,365 B1 | 10/2002 | Aoki et al. |
| 6,464,986 B1 | 10/2002 | Aoki et al. |
| 6,623,742 B2 | 9/2003 | Voet |
| 2003/0224019 A1 | 12/2003 | O'Brien et al. |
| 2004/0208889 A1 * | 10/2004 | Sutton et al. ............ 424/190.1 |

FOREIGN PATENT DOCUMENTS

| | | |
|---|---|---|
| DE | 101 50 415 A1 | 5/2003 |
| WO | WO 03/0011333 | 2/2003 |

OTHER PUBLICATIONS

Francis, J.W., et al. 1995. J. Biol. Chem. 270(25): 15434-15442.*
O'Sullivan, G.A., et al. 1999. J. Biol. Chem. 274(52): 36897-36904.*
U.S. Appl No. 10/429,069, filed May 2, 2003, Voet et al.
U.S. Appl. No. 10/630,587, filed Jul. 29, 2003, Aoki et al.
U.S. Appl. No. 10/731,973, filed Dec. 9, 2003, First.
U.S. Appl. No. 10/752,869, filed Jan. 6, 2004, First.
U.S. Appl. No. 10/423,380, filed Apr. 25, 2003, Ackerman et al.
U.S. Appl. No. 10/194,805, filed Jul. 11, 2002, Donovan.

U.S. Appl. No. 09/315,298, filed May 20, 1999, Teng et al.
Carmen Gonelle-Gispert et al., "SNAP-25a and -25b isoforms are both expressed in insulin-secreting cells and can function in insulin secretion," Biochem. J. (1999) 339 (159-165).
Moyer et al., "Therapy With Botulinum Toxin," *Botilum Toxin Type B: Experimental And Clinical Experience*, 1994, Chapter 6, pp. 71-85.
Habermann et al., "Tetanus toxin and botulinum A and C neurotoxins inhibit noradrenaline release from cultured mouse brain," *J Neurochem.* Aug. 1988;51(2):522-7.
Sanchez-Prieto et al., "Botulinum Toxin A Blocks Glutamate Exocytosis From Guinea Pig Cerebral Cortical Synaptosomes,". *Eur. J. Biochem,* 1897, vol. 165, pp. 675-681.
Pearce, "Pharmacologic Characterization Of Botulinum Toxin For Basic Science And Medicine," *Toxicon* (1997) vol. 35(9), pp. 1373-1412 at 1393.
Bigalke et al., "Botulinum A Neurotoxin Inhibits Non-Cholinergic Synaptic Transmission In Mouse Spinal Cord Neurons In Culture," *Brain Research,* 1985, vol. 360, pp. 318-324.
Habermann, "Inhibition By Tetanus And Botulinum A Toxin Of The Release Of [3H]Noradrenaline And [3H]GABA From Rat Brain Homogenate," *Experientia,* 1988, vol. 44, pp. 224-226.
Bigalke et al., "Tetanux Toxin And Botulinum A Toxin Inhibit Release And Uptake Of Various Transmitters," 1981, *Naunyn-Schmiedeberg Arch. Pharmacol,* vol. 316, pp. 244-251.
Jankovic et al., "Therapy With Botulinum Toxin," *Marcel Dekker, Inc.,* 1994, p. 5.
Schantz et al., "Properties And Use Of Botulinum Toxin And Other Microbial Neurotoxins In Medicine," *Microbiol Rev.,* 1992, vol. 56, pp. 80-99.
Naumann et al., Botulinum toxin type A in the treatment of focal, axillary and palmar hyperhidrosis and other hyperhidrotic conditions, *European J. Neurology,* 1999, vol. 6, Supp. 4, 111-115.
Bushara, "Botulinum Toxin And Rhinorrhea," *Otolaryngol Head Neck Surg.,* 1996, vol. 114, No. 3, p. 507.
Ragona et al., "Management of Parotid Sialocele with Botulinum Toxin," *The Laryngoscope,* 1999, vol. 109, pp. 1344-1346.

(Continued)

Primary Examiner—Karen Cochrane Carlson
Assistant Examiner—Marsha Tsay
(74) Attorney, Agent, or Firm—Dean G. Stathakis; Martin A. Voet; Joel B. German

(57) ABSTRACT

The present invention provides for methods of modulating the degradation rate of a toxin in a cell, thereby modulating the half-life of the toxin. Particularly, the invention features methods of modulating the degradation rate of a toxin by modulating fusion between a lysosome and an endosome that carries the toxin in the cell.

4 Claims, No Drawings

OTHER PUBLICATIONS

Wiegand et al., "[125]I-labelled botulinum a neurotoxin: pharmacokinetics in cats after intramuscular injection," *Naunyn-Schmiedeberg's Arch. Pharmacol.* (1976) 292:161-165.

Habermann "[125]I-labelled neurotoxin from clostridium Botulinum a: preparation, binding to synaptosomes and ascent to the spinal cord," *Naunyn-Schmiedeberg's Arch. Pharmacol.* (1974) 281:58-56.

Murry et al., "Spasmodic dysphonia. Emotional status and botulinum toxin treatment," *Arch Otolaryngol Head Neck Surg.,* Mar. 1994;120(3):310-6.

Jahanshahi et al., "Psychological functioning before and after treatment of torticollis with botulinum toxin," *J Neurol Neurosurg Psychiatry,* Mar. 1992;55(3):229-31.

Bhattacharya et al., "Novel Uses Of Botulinum Toxin Type A: Two Case Reports," *Mov Disord.,* 2000, vol. 15, pp. 51-52.

Payne et al., "Botulinum Toxin As A Novel Treatment For Self Multilation In Lesch-Nyhan Syndrome," *Ann. Neurol.,* 2002, vol. 52, p. 157.

Blugerman et al., "Multiple Eccrine Hidrocystomas: A New Therapeutic Option With Botulinum Tpxom," *Dermatol. Surg.,* 2003, vol. 29, pp. 557-559.

Jost, "Ten Years' Experience With Botulinum Toxin In Anal Fissure," *Int. J. Colorectal Dis.,* 2002, vol. 17, No. 5, pp. 298-302.

Heckmann et al., "Botulinum Toxin Type A Injection In The Treatment Of Lichen Simplex: An Open Pilot Study," *J. Am. Acad. Dermatol.,* 2002, vol. 46, No. 4, pp. 617-619.

Aoki et al., "Mechanisms Of The Antinociceptive Effect Of Subcutaneous Botox: Inhibition Of Peripheral And Central Nociceptive Processing," *Cephalagia* 2003, vol. 23, No. 7, p. 649.

Li et al., "Sensory And Motor Denervation Influences Epidermal Thickness In Rat Foot Glabrous Skin," *Exp. Neurol,* 1997, vol. 147, pp. 452-462.

Katsambas et al., "Cutaneous Diseases Of The Foot: Unapproved Treatments," *Clin. Dermatol.,* 2002, pp. 689-699.

Sevim et al., "Botulinum Toxin-A Therapy For Palmar And Plantar Hyperhidrosis," *Acta Neurol. Belg.,* 2002, vol. 102, No. 4, pp. 167-170.

Suputtitada, "Local Botulinum Toxin Type A Injections In The Treatment Of Spastic Toes," *Am. J. Phys. Med. Rehabil.,* 2002, vol. 81, No. 10, pp. 770-775.

Tacks et al., "Idiopathic Toe Walking: Treatment With Botulinum Toxin A Injection," *Dev. Med. Child Neurol.,* 2002, vol. 44, p. 6.

Rogers et al., "Injections Of Botulinum Toxin A In Foot Dystonia," *Neurology,* 1993, p. 43.

Binz et al., "The Complete Sequence Of Botulinum Neurotoxin Type A And Comparison With Other Clostridial Neurotoxins," *J. Biological Chemistry,* 1990, vol. 265, No. 16, pp. 9153-9158.

Luzio et al., "Lysosome-endosome fusion and lysosome biogenesis," *J Cell Sci.,* May 2000;113 (Pt 9):1515-24.

Fujita et al., "A dominant negative form of the AAA ATPase SKD1/VPS4 impairs membrane trafficking out of endosomal/lysosomal compartments: class E vps phenotype in mammalian cells" *J Cell Sci.,* Jan. 15, 2003;116(Pt 2):401-14.

Peters et al., "Control of the terminal step of intracellular membrane fusion by protein phosphatase 1," *Science,* Aug. 13, 1999;285(5430):1084-7.

Mousavi et al., "Phosphoinositide 3-kinase regulates maturation of lysosomes in rat hepatocytes," Biochem J. Jun. 15, 2003;372(Pt 3):861-9.

Zucker et al., "Rapid trafficking of membrane type 1-matrix metalloproteinase to the cell surface regulates progelatinase A activation" *Lab Invest.,* 2002, vol. 82, No. 12, pp. 1673-1684.

Ramm et al., "Pathways of intracellular trafficking and release of ferritin by the liver in vivo: the effect of chloroquine and cytochalasin D," Hepatology. Feb. 19, 1994;(2):504-13.

Al-Jaufy et al., "Purification and characterization of a shiga toxin a subunit-CD4 fusion protein cytotoxic to human immunodeficiency virus-infected cells," *Infection and Immunity* (1995) 63(8):3073-3078.

Ohashi et al., "An arrested late endosome-lysosome intermediate aggregate observed in a Chinese hamster ovary cell mutant isolated by novel three-step screening," *J. of Cell Science* (1999) 112:1125-1138.

Huete-Pérez et al., "Protease trafficking in two primitive eukaryotes is mediated by a prodomain protein motif*," *The Journal of Biological Chemistry* (1999) 274(23):16249-16256.

Ruepp et al., "Proteasome function is dispensable under normal but not under heat shock conditions in *Thermoplasma acidophilum,*" *FEBS Letters* (1998) 425:87-90.

Ramachandran et al., "Structural insights into the membrane-anchoring mechanism of a cholesterol-dependent cytolysin," *Nature Structural Biology* (2002) 9(11):823-827.

Miyata et al., "*Clostridium perfringers* ε-toxin forms a heptameric pore within the detergent-insoluble microdomains of madin-darby canine kidney cells and rat synaptosomes*," *The Journal of Biological Chemistry* (2002) 277(42):39463-39468.

* cited by examiner

METHODS OF MODULATING INTRACELLULAR DEGRADATION RATES OF TOXINS

FIELD OF INVENTION

This invention broadly relates to intracellular trafficking. Particularly, the invention relates to methods of modulating the degradation rates of toxins in a cell.

BACKGROUND

The genus *Clostridium* has more than one hundred and twenty seven species, grouped according to their morphology and functions. The anaerobic, gram positive bacterium *Clostridium botulinum* produces a potent polypeptide neurotoxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and shows a high affinity for cholinergic motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of a commercially available botulinum toxin type A (purified neurotoxin complex, available from Allergan, Inc., of Irvine, Calif. under the trade name BOTOX® in 100 unit vials) is a LD50 in mice (i.e. 1 unit). One unit of BOTOX® contains about 50 picograms (about 56 attomoles) of botulinum toxin type A complex. Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins*, pages 63–84 (chapter 4) of Natural Toxins II, edited by B. R. Singh et al., Plenum Press, New York (1976) (where the stated LD50 of botulinum toxin type A of 0.3 ng equals 1 U is corrected for the fact that about 0.05 ng of BOTOX® equals 1 unit). One unit (U) of botulinum toxin is defined as the LD50 upon intraperitoneal injection into female Swiss Webster mice weighing 18 to 20 grams each.

Seven generally immunologically distinct botulinum toxins have been characterized, these being respectively botulinum toxin serotypes A, B, $C_1$, is D, E, F and G each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate LD50 for botulinum toxin type A. Moyer E et al., *Botulinum Toxin Type B: Experimental and Clinical Experience*, being chapter 6, pages 71–85 of "Therapy with Botulinum Toxin", edited by Jankovic, J. et al. (1994), Marcel Dekker, Inc. Botulinum toxin apparently binds with high affinity to cholinergic motor neurons, is translocated into the neuron and blocks the release of acetylcholine. Additional uptake can take place through low affinity receptors, as well as by phagocytosis and pinocytosis.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain (the H chain or HC) and a cell surface receptor. The receptor is thought to be different for each type of botulinum toxin and for tetanus toxin. The carboxyl end segment of the HC appears to be important for targeting of the botulinum toxin to the cell surface.

In the second step, the botulinum toxin crosses the plasma membrane of the target cell. The botulinum toxin is first engulfed by the cell through receptor-mediated endocytosis, fused with an endosome and an endosome containing the botulinum toxin is formed. The toxin then escapes the endosome into the cytoplasm of the cell. This step is thought to be mediated by the amino end segment of the HC, the $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the botulinum toxin to embed itself in the endosomal membrane. The botulinum toxin (or at least the light chain of the botulinum) then translocates through the endosomal membrane into the cytoplasm.

The last step of the mechanism of botulinum toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc ($Zn^{++}$) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Botulinum toxin serotype A and E cleave SNAP-25. Botulinum toxin serotype C1 was originally thought to cleave syntaxin, but was found to cleave syntaxin and SNAP-25. Each of the botulinum toxins specifically cleaves a different bond, except botulinum toxin type B (and tetanus toxin) which cleave the same bond. Each of these cleavages block the process of vesicle-membrane docking, thereby preventing exocytosis of vesicle content.

Botulinum toxins have been used in clinical settings for the treatment of neuromuscular disorders characterized by hyperactive skeletal muscles (i.e. motor disorders). In 1989 a botulinum toxin type A complex was approved by the U.S. Food and Drug Administration for the treatment of blepharospasm, strabismus and hemifacial spasm. Subsequently, a botulinum toxin type A was also approved by the FDA for the treatment of cervical dystonia and for the treatment of glabellar lines, and a botulinum toxin type B was approved for the treatment of cervical dystonia. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about three months, although significantly longer periods of therapeutic activity have been reported.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type C1 has been shown to cleave both syntaxin and SNAP-25. These differences in mechanism of action may affect the relative potency and/or duration of action of the various botulinum toxin serotypes.

Apparently, a substrate for a botulinum toxin can be found in a variety of different cell types. See e.g. *Biochem J* 1;339 (pt 1):159–65:1999, and *Mov Disord,* 10(3):376:1995 (pancreatic islet B cells contains at least SNAP-25 and synaptobrevin).

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and C1 is apparently produced as only a 700 kD or 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin proteins and a non-toxin and non-toxic non-hemaglutinin protein. These two non-toxin proteins (which along with the botulinum toxin molecule comprise the relevant neurotoxin complex) may act to provide stability against denaturation to the botulinum toxin molecule and protection against digestive acids when a botulinum toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine (Habermann E., et al., *Tetanus Toxin and Botulinum A and C Neurotoxins Inhibit Noradrenaline Release From Cultured Mouse Brain,* J Neurochem 51 (2);522–527:1988) CGRP, substance P and glutamate (Sanchez-Prieto, J., et al., *Botulinum Toxin A Blocks Glutamate Exocytosis From Guinea Pig Cerebral Cortical Synaptosomes,* Eur J. Biochem 165;675–681:1897. Thus, when adequate concentrations are used, stimulus-evoked release of most neurotransmitters can be blocked by botulinum toxin. See e.g. Pearce, L. B., *Pharmacologic Characterization of Botulinum Toxin For Basic Science and Medicine,* Toxicon 35(9);1373–1412 at 1393; Bigalke H., et al., *Botulinum A Neurotoxin Inhibits Non-Cholinergic Synaptic Transmission in Mouse Spinal Cord Neurons in Culture,* Brain Research 360;318–324:1985; Habermann E., *Inhibition by Tetanus and Botulinum A Toxin of the release of [3H]Noradrenaline and [3H]GABA From Rat Brain Homogenate,* Experientia 44;224–226:1988, Bigalke H., et al., *Tetanus Toxin and Botulinum A Toxin Inhibit Release and Uptake of Various Transmitters, as Studied with Particulate Preparations From Rat Brain and Spinal Cord, Naunyn-Schmiedeberg's* Arch Pharmacol 316;244–251:1981, and; Jankovic J. et al., *Therapy With Botulinum Toxin,* Marcel Dekker, Inc., (1994), page 5.

Botulinum toxin type A can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes C1, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

High quality crystalline botulinum toxin type A can be produced from the Hall A strain of *Clostridium botulinum* with characteristics of $\geq 3 \times 10^7$ U/mg, an A260/A278 of less than 0.60 and a distinct pattern of banding on gel electrophoresis. The known Shantz process can be used to obtain crystalline botulinum toxin type A, as set forth in Shantz, E. J., et al, *Properties and use of Botulinum toxin and Other Microbial Neurotoxins in Medicine,* Microbiol Rev. 56;80–99:1992. Generally, the botulinum toxin type A complex can be isolated and purified from an anaerobic fermentation by cultivating *Clostridium botulinum* type A in a suitable medium. The known process can also be used, upon separation out of the non-toxin proteins, to obtain pure botulinum toxins, such as for example: purified botulinum toxin type A with an approximately 150 kD molecular weight with a specific potency of $1–2 \times 10^8$ LD50 U/mg or greater; purified botulinum toxin type B with an approximately 156 kD molecular weight with a specific potency of $1–2 \times 10^8$ LD50 U/mg or greater, and; purified botulinum toxin type F with an approximately 155 kD molecular weight with a specific potency of $1–2 \times 10^7$ LD50 U/mg or greater.

Botulinum toxins and/or botulinum toxin complexes can be obtained from List Biological Laboratories, Inc., Campbell, Calif.; the Centre for Applied Microbiology and Research, Porton Down, U.K.; Wako (Osaka, Japan), Metabiologics (Madison, Wis.) as well as from Sigma Chemicals of St Louis, Mo. Pure botulinum toxin can also be used to prepare a pharmaceutical compound.

As with enzymes generally, the biological activities of the botulinum toxins (which are intracellular peptidases) is dependent, at least in part, upon their three dimensional conformation. Thus, botulinum toxin type A is detoxified by heat, various chemicals surface stretching and surface drying. Additionally, it is known that dilution of a botulinum toxin complex obtained by the known culturing, fermentation and purification to the much, much lower toxin concentrations used for pharmaceutical compound formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the botulinum toxin may be used months or years after the toxin containing pharmaceutical compound is formulated, the toxin can be stabilized with a stabilizing agent such as albumin and gelatin.

A commercially available botulinum toxin containing pharmaceutical compound is sold under the trademark BOTOX® (available from Allergan, Inc., of Irvine, Calif.). BOTOX® consists of a purified botulinum toxin type A complex, albumin and sodium chloride packaged in sterile, vacuum-dried form. The botulinum toxin type A is made from a culture of the Hall strain of *Clostridium botulinum* grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C. BOTOX® can be reconstituted with sterile, non-preserved saline prior to intramuscular injection. Each vial of BOTOX® contains about 100 units (U) of *Clostridium botulinum* toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative; (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2° C. to about 8° C. Reconstituted, refrigerated BOTOX® has been reported to retain its potency for at least about two weeks. *Neurology*, 48:249–53: 1997.

It has been reported that botulinum toxin type A has been used in clinical settings as follows:

(1) about 75–125 units of BOTOX® per intramuscular injection (multiple muscles) to treat cervical dystonia;
(2) 5–10 units of BOTOX® per intramuscular injection to treat glabellar lines (brow furrows) (5 units injected intramuscularly into the procerus muscle and 10 units injected intramuscularly into each corrugator supercilii muscle);
(3) about 30–80 units of BOTOX® to treat constipation by intrasphincter injection of the puborectalis muscle;
(4) about 1–5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.
(5) to treat strabismus, extraocular muscles have been injected intramuscularly with between about 1–5 units of BOTOX®, the amount injected varying based upon both the size of the muscle to be injected and the extent of muscle paralysis desired (i.e. amount of diopter correction desired).
(6) to treat upper limb spasticity following stroke by intramuscular injections of BOTOX® into five different upper limb flexor muscles, as follows:
  (a) flexor digitorum profundus: 7.5 U to 30 U
  (b) flexor digitorum sublimus: 7.5 U to 30 U
  (c) flexor carpi ulnaris: 10 U to 40 U
  (d) flexor carpi radialis: 15 U to 60 U
  (e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.
(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

It is known that botulinum toxin type A can have an efficacy for up to 12 months (*European J. Neurology* 6 (Supp 4): S111–S1150:1999), and in some circumstances for as long as 27 months, when used to treat glands, such as in the treatment of hyperhydrosis . See e.g. Bushara K., *Botulinum toxin and rhinorrhea*, Otolaryngol Head Neck Surg 1996; 114(3):507, and *The Laryngoscope* 109:1344–1346:1999. However, the usual duration of an intramuscular injection of BOTOX® is typically about 3 to 4 months.

The success of botulinum toxin type A to treat a variety of clinical conditions has led to interest in other botulinum toxin serotypes. Two commercially available botulinum type A preparations for use in humans are BOTOX® available from Allergan, Inc., of Irvine, Calif., and Dysport® available from Beaufour Ipsen, Porton Down, England. A botulinum toxin type B preparation (MyoBloc®) is available from Elan Pharmaceuticals of San Francisco, Calif.

In addition to having pharmacologic actions at the peripheral location, botulinum toxins may also have inhibitory effects in the central nervous system. Work by Weigand et al, *Nauny-Schmiedeberg's Arch. Pharmacol.* 1976; 292, 161–165, and Habermann, *Nauny-Schmiedeberg's Arch. Pharmacol.* 1974; 281, 47–56 showed that botulinum toxin is able to ascend to the spinal area by retrograde transport. As such, a botulinum toxin injected at a peripheral location, for example intramuscularly, may be retrograde transported to the spinal cord.

U.S. Pat. No. 5,989,545 discloses that a modified clostridial neurotoxin or fragment thereof, preferably a botulinum toxin, chemically conjugated or recombinantly fused to a particular targeting moiety can be used to treat pain by administration of the agent to the spinal cord.

It has been reported that use of a botulinum toxin to treat various spasmodic muscle conditions can result in reduced depression and anxiety, as the muscle spasm is reduced. Murry T., et al., *Spasmodic dysphonia; emotional status and botulinum toxin treatment*, Arch Otolaryngol 1994 March; 120(3): 310–316; Jahanshahi M., et al., *Psychological functioning before and after treatment of torticollis with botulinum toxin*, J Neurol Neurosurg Psychiatry 1992; 55(3): 229–231. Additionally, German patent application DE 101 50 415 A1 discusses intramuscular injection of a botulinum toxin to treat depression and related affective disorders. A botulinum toxin has also been proposed for or has been used to treat skin wounds (U.S. Pat. No. 6,447,787), various autonomic nerve dysfunctions (U.S. Pat. No. 5,766,605), tension headache, (U.S. Pat. No. 6,458,365), migraine headache pain (U.S. Pat. No. 5,714,468), sinus headache (U.S. patent application Ser. No. 429,069), post-operative pain and visceral pain (U.S. Pat. No. 6,464,986), neuralgia pain (U.S. patent application Ser. N. 630,587), hair growth and hair retention (U.S. Pat. No. 6,299,893), dental related ailments (U.S. provisional patent application Ser. No. 60/418,789), fibromyalgia (U.S. Pat. No. 6,623,742), various skin disorders (U.S. patent application Ser. No. 10/731,973), motion sickness (U.S. patent application serial number 752,869), psoriasis and dermatitis (U.S. Pat. No. 5,670,484), injured muscles (U.S. Pat. No. 6,423,319) various cancers (U.S. Pat. No. 6,139,845), smooth muscle disorders (U.S. Pat. No. 5,437,291), down turned mouth corners (U.S. Pat. No. 6,358,917), nerve entrapment syndromes (U.S. patent application 2003 0224019), various impulse disorders (U.S. patent application Ser. No. 423,380), acne (WO 03/011333) and neurogenic inflammation (U.S. Pat. No. 6,063,768). Controlled release toxin implants are known (see e.g. U.S. Pat. Nos. 6,306,423 and 6,312,708) as is transdermal botulinum toxin administration (U.S. patent application Ser. No. 10/194,805).

Botulinum toxin type A has been used to treat epilepsia partialis continua, a type of focal motor epilepsy. Bhattacharya K., et al., *Novel uses of botulinum toxin type A: two case reports*, Mov Disord 2000; 15(Suppl 2):51–52.

It is known that a botulinum toxin can be used to: weaken the chewing or biting muscle of the mouth so that self inflicted wounds and resulting ulcers can heal (Payne M., et al, *Botulinum toxin as a novel treatment for self mutilation in Lesch-Nyhan syndrome*, Ann Neurol 2002 September; 52(3 Supp 1):S157); permit healing of benign cystic lesions or tumors (Blugerman G., et al., *Multiple eccrine hidrocystomas: A new therapeutic option with botulinum toxin*, Dermatol Surg 2003 May;29(5):557-9); treat anal fissure (Jost W., *Ten years' experience with botulinum toxin in anal fissure*, Int J Colorectal Dis 2002 September;17(5):298–302, and; treat certain types of atopic dermatitis (Heckmann M., et al., *Botulinum toxin type A injection in the treatment of lichen simplex: An open pilot study*, J Am Acad Dermatol 2002 April;46(4):617–9).

Additionally, a botulinum toxin may have an effect to reduce induced inflammatory pain in a rat formalin model. Aoki K., et al, *Mechanisms of the antinociceptive effect of subcutaneous Botox: Inhibition of peripheral and central nociceptive processing*, Cephalalgia 2003 September;23(7): 649. Furthermore, it has been reported that botulinum toxin nerve blockage can cause a reduction of epidermal thickness. Li Y, et al., *Sensory and motor denervation influences epidermal thickness in rat foot glabrous skin*, Exp Neurol 1997;147:452–462 (see page 459). Finally, it is known to administer a botulinum toxin to the foot to treat excessive foot sweating (Katsambas A., et al., *Cutaneous diseases of the foot: Unapproved treatments*, Clin Dermatol 2002 November–December;20(6):689–699; Sevim, S., et al., *Botulinum toxin-A therapy for palmar and plantar hyperhidrosis*, Acta Neurol Belg 2002 December;102(4):167–70), spastic toes (Suputtitada, A., *Local botulinum toxin type A injections in the treatment of spastic toes*, Am J Phys Med Rehabil 2002 October;81(10):770–5), idiopathic toe walking (Tacks, L., et al., *Idiopathic toe walking: Treatment with botulinum toxin A injection*, Dev Med Child Neurol 2002; 44(Suppl 91):6), and foot dystonia (Rogers J., et al., *Injections of botulinum toxin A in foot dystonia*, Neurology 1993 April;43(4 Suppl 2)).

Tetanus toxin, as wells as derivatives (i.e. with a non-native targeting moiety), fragments, hybrids and chimeras thereof can also have therapeutic utility. The tetanus toxin bears many similarities to the botulinum toxins. Thus, both the tetanus toxin and the botulinum toxins are polypeptides made by closely related species of *Clostridium* (*Clostridium tetani* and *Clostridium botulinum*, respectively). Additionally, both the tetanus toxin and the botulinum toxins are dichain proteins composed of a light chain (molecular weight about 50 kD) covalently bound by a single disulfide bond to a heavy chain (molecular weight about 100 kD). Hence, the molecular weight of tetanus toxin and of each of the seven botulinum toxins (non-complexed) is about 150 kD. Furthermore, for both the tetanus toxin and the botulinum toxins, the light chain bears the domain which exhibits intracellular biological (protease) activity, while the heavy chain comprises the receptor binding (immunogenic) and cell membrane translocational domains.

Further, both the tetanus toxin and the botulinum toxins exhibit a high, specific affinity for gangliocide receptors on the surface of presynaptic cholinergic neurons. Receptor mediated endocytosis of tetanus toxin by peripheral cholinergic neurons results in retrograde axonal transport, blocking of the release of inhibitory neurotransmitters from central synapses and a spastic paralysis. Contrarily, receptor mediated endocytosis of botulinum toxin by peripheral cholinergic neurons results in little if any retrograde transport, inhibition of acetylcholine exocytosis from the intoxicated peripheral motor neurons and a flaccid paralysis.

Finally, the tetanus toxin and the botulinum toxins resemble each other in both biosynthesis and molecular architecture. Thus, there is an overall 34% identity between the protein sequences of tetanus toxin and botulinum toxin type A, and a sequence identity as high as 62% for some functional domains. Binz T. et al., *The Complete Sequence of Botulinum Neurotoxin Type A and Comparison with Other Clostridial Neurotoxins*, J Biological Chemistry 265(16); 9153–9158:1990.

Acetylcholine

Typically only a single type of small molecule neurotransmitter is released by each type of neuron in the mammalian nervous system, although there is evidence which suggests that several neuromodulators can be released by the same neuron. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the bag 1 fibers of the muscle spindle fiber, by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephrine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large densecore vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

One of the reasons that BoNT/A has been selected over the other serotypes, for example serotypes B, $C_1$, D, E, F, and G, for clinical use is that BoNT/A has a substantially longer lasting therapeutic effect. In other words, the inhibitory effect of BoNT/A is more persistent. Therefore, the other serotypes of botulinum toxins could potentially be effectively used in a clinical environment if their half-lives in the mammal are enhanced. For example, parotid sialocele is a condition where the patient suffers from excessive salivation. It is known that serotype D may be very effective in reducing excessive salivation. However, the half-life of serotype D botulinum toxin is relatively short and thus may not be practical for clinical use. If the half-lilfe of serotype D may be enhanced, it may effectively be used in a clinical environment to treat, for example, parotid sialocele.

Another reason that BoNT/A has been a preferred neurotoxin for clinical use is, as discussed above, its superb ability to immobilize muscles through flaccid paralysis. For example, BoNT/A is preferentially used to immobilize muscles and prevent limb movements after a tendon surgery to facilitate recovery. However, for some minor tendon surgeries, the healing time is relatively short. It would be beneficial to be able to use BoNT/A without the prolonged persistence for use in such circumstances so that the patient can regain mobility at about the same time they recover from the surgery. Thus, there is a need to have methods of modulating the degradation rates or half-lives of neurotoxins.

SUMMARY OF THE INVENTION

The present invention provides for such unmet medical need as described above. Accordingly, the present invention provides for methods of modulating the degradation rate of a toxin in a cell. In some embodiments, modulating the degradation rate of a toxin comprises modulating fusion between a lysosome and an endosome that carries the toxin in the cell. In some embodiments, lysosome-endosome fusion modulators may be used. For example, a lysosome-endosome fusion inhibitor may be used to inhibit the fusion, and thereby decrease the degradation rate of the toxin in the cell; and a lysosome-endosome fusion facilitator may be used to facilitate the fusion, and thereby increase the degradation rate of the toxin in the cell.

The present invention also features methods of modulating the half-lives of toxins in a mammal. In some embodiments, the methods comprise co-administering to the mammal a toxin with a compound that modulates fusion of a lysosome and an endosome. The present invention also provides for methods of treating a biological disorder in a patient, for example, by co-administering to a patient in need thereof a toxin and a lysosome-endosome fusion inhibitor.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

Definitions

"About" means approximately or nearly and in the context of a numerical value or range set forth herein means ±10% of the numerical value or range recited or claimed.

"Locally administering" means direct administration of a pharmaceutic at or to the vicinity of a site on or within an animal body, at which site a biological effect of the pharmaceutic is desired. Local administration excludes systemic routes of administration, such as intravenous or oral administration.

DESCRIPTION OF EMBODIMENTS

The present invention relates to methods of modulating the degradation rate of a toxin in a cell. The invention is based, in part, upon the discovery that modulating fusion between a lysosome and an endosome that carries the toxin in the cell affects the degradation rate of the toxin. Toxins that are within the scope of the present invention include beratti toxin, butyricum toxin, tetani toxin, BoNT/A, B, $C_1$, D, E, F, and G. In some embodiments, the present invention relates to methods of modulating the degradation rate of a botulinum toxin in a cell.

Lysosomes are membrane bound organelles containing many hydrolytic enzymes, which are optimally active at an acid pH. They are distinguished from endosomes by the presence of the two mannose-6-phosphate receptors (MPRs) and recycling cell surface receptors. They are characteristically observed by electron microscopy to be organelles of about 0.5 um diameter and often have electron-dense cores. Lysosomes are often regarded as the terminal degradation compartment of the endocytic pathway, and play important roles in the degradation of phagocytosed material, in autophagy, in crinophagy, and in the proteolysis of cyotsolic proteins transported across the lysosomal membrane by a carrier mediated mechanism.

As discussed above, toxins (e.g., botulinum toxins) are endocytosed into a cell, and reside in an endosome therein. Without wishing to limit the invention to any theory or mechanism of operation, it is believed that toxins in the cells are subjected to degradation when the endosome fuses with the lysosome. Further, it is believed that lysosomes are able to fuse directly with late endosomes to form hybrid organelles in which degradation of the endocytosed material (e.g., a toxin such as a botulinum toxin) takes place, and form which lysosomes are reformed.

The fusion between the lysosome and the endosome is ATP, cytosol and temperature dependent. See Luzio J. P. et al., J. Cell Science, 113:1515–1524 (2000), the disclosure of which is incorporated in its entirety by reference herein. The fusion also requires the presence of NSF (N-ethylmaleimide sensitive factor) and SNAPs (soluble NSF attachment proteins) and is inhibited by Rab-GDI (GDP dissociation inhibitor). This implies that Rab GTPase is necessary for the fusion between the lysosome and the endosome.

In some embodiments, the invention provides for a method of decreasing (i.e., modulating) the degradation rate of a toxin in a cell. In some embodiments, the method of decreasing the degradation of a toxin in a cell comprises introducing a lysosome-endosome fusion inhibitor into the cell to prevent the fusion of the lysosome with the endosome. The lysosome-endosome fusion inhibitor may be introduced into the cell through any means known by one of ordinary skill in the art. For example, the lysosome-endosome inhibitor may be introduced into the cell through the use of electroporation techniques. Since the fusion between the lysosome and the endosome may be dependent on GTP and ATP, a lysosome-endosome fusion inhibitor may comprise a GTPase inhibitor, an ATPase inhibitor or mixtures thereof. See Luzio J. P. et al., J. Cell Science, 113: 1515–1524 (2000); and Fujita H. et al., J. Cell Science, 116: 401–414 (2003), the disclosures of which are incorporated in their entirety by reference herein. Other lysosome-endosome fusion inhibitors include the serine-threonine phosphatase inhibitor microcystin LR, mastoparan, and guanosine 5'-O-(3'-thiotriphosphate) (Peters et al., Science, Vol 285, Issue 5430,1084–1087, 13 Aug. 1999), Wortmannin (Biochem. J. (2003) 372 (861–869) (Printed in Great Britain)), brefeldin A (Golgi complex disrupter), cytochalasin B (mircrofilament inhibitor), cytochalasin D, an inhibitor of actin filaments, PMA (phorbol 12-myristate 13-acetate), a stimulator of protein kinase C, and bafilomycin A, an inhibitor of lysosome/endosome function (Zuckers et al., Lab Invest. 2002 December;82(12):1673–84; and Ramm et al., Hepatology, 1994 February;19(2):504–13.)

Intracellular membrane fusion can be divided into distinct subreactions: priming, tethering and docking of the membranes, and subsequent mixing of the bilayers and contents Most components identified so far, such as NSF (NEM-sensitive fusion protein), α-SNAP (soluble NSF attachment protein), SNAREs (SNAP receptors), Rab-like guanosine triphosphatases (GTPases) and their cofactors, and the LMA1 complex (low molecular weight activity), act in the early steps of intracellular membrane fusion, mediating recognition and association of the appropriate membranes. In contrast, there is little information about the transition from docking to bilayer mixing.

In some embodiments, GTPase inhibitors of the present invention comprise a Rab GTPase inhibitor, a Rho GTPase inhibitor, or a mixture thereof. In some embodiments, ATPase inhibitors of the present invention comprise an ATPase associated with cellular activities (AAA) type inhibitor. These inhibitors are commonly known by one of ordinary skill in the art.

Non-limiting examples of GTPase inhibitors of the present invention include a guanine dissociation inhibitor (GDI) protein, an isoprene binding domain of the guanine dissociation inhibitor, a GAP protein, an $AlF_4—$, a guanylyl 5-thiophosphate, a Y-27632, a C3 transferase, a *Clostridium difficile* toxin A, a *Clostridium difficile* toxin B, a *Clostridium. sordellii* lethal toxin LT, a *Escherichia coli* cytotoxic necrotizing factor 1 (CNF1), a *Escherichia coli* cytotoxic necrotizing factor 2 (CNF2) and a *Bordetella bronchiseptica* dermonecrotizing toxin (DNT).

In some embodiments, the use of a lysosome-endosome fusion inhibitor is effective to decrease the degradation rate of a toxin (e.g., botulinum toxin) by about more than 10%. In some embodiments, the use of a lysosome-endosome fusion inhibitor is effective to decrease the degradation rate of a toxin (e.g., botulinum toxin) by about more than 25%. In some embodiments, the use of a lysosome-endosome fusion inhibitor is effective to decrease the degradation rate of a toxin (e.g., botulinum toxin) by about more than 50%. In some embodiments, the use of a lysosome-endosome fusion inhibitor is effective to decrease the degradation rate of a toxin (e.g., botulinum toxin) by about more than 100%.

In some embodiments, the invention provides for a method of increasing (i.e., modulating) the degradation rate of a toxin, e.g., a botulinum toxin, in a cell. In some embodiments, the method of increasing the degradation of a botulinum toxin in a cell comprises introducing a lysosome-endosome fusion facilitator into the cell to enhance the fusion of the lysosome with the endosome. In some embodiments, a fusion facilitator comprises a GTPase activator, a type III secreted toxin, and ammonium chloride (lysosome stablizers).

In some embodiments, the GTPase activator activator of the present invention comprises a GEF protein, GEF protein mimic, or mixtures thereof.

In some embodiments, the type III secreted toxin is a *Salmonella typhimurium* SopE, a *Salmonella* SptP, a *Yersinia pseudotubercolosis* YopE, a *Yersinia* YopT or a *Pseudomonas aeruginosa* ExoS.

In some embodiments, the use of a lysosome-endosome fusion facilitator is effective to increase the degradation rate of a toxin (e.g., botulinum toxin) by about more than 10%. In some embodiments, the use of a lysosome-endosome fusion facilitator is effective to increase the degradation rate of a toxin (e.g., botulinum toxin) by about more than 25%. In some embodiments, the use of a lysosome-endosome fusion facilitator is effective to increase the degradation rate of a toxin (e.g., botulinum toxin) by about more than 50%. In some embodiments, the use of a lysosome-endosome fusion facilitator is effective to increase the degradation rate of a toxin (e.g., botulinum toxin) by about more than 100%.

The present invention also features a method for modulating the half-life of a botulinum toxin in a mammal. As used herein, "half-life" refers to the time it takes for half of the toxin population to be degraded in a mammal. In some embodiments, the method comprises co-administering to the mammal a toxin with a compound that modulates fusion of a lysosome and an endosome. As used herein, "co-administering" includes sequential administration of botulinum toxin followed by lysosome-endosome fusion modulator, sequential administration of a lysosome-endosome fusion modulator followed by a botulinum toxin, or simultaneous administration of a botulinum toxin and a lysosome-endosome fusion modulator.

In some embodiments, the present invention provides for a method of increasing (i.e., modulating) the half-life of the toxin in a mammal. For example, the method of increasing the half-life of the toxin comprises co-administering to the mammal the toxin and a lysosome-endosome fusion inhibitor. In some embodiments, the lysosome-endosome fusion inhibitor comprises a GTPase inhibitor, an ATPase inhibitor, brefeldin A (Golgi complex disrupter), cytochalasin B (mircrofilament inhibitor), Wortmannin, cytochalasin D, an inhibitor of actin filaments, PMA, a stimulator of protein kinase C, and bafilomycin A, an inhibitor of lysosome/endosome function.

In some embodiments, the GTPase inhibitor comprises a guanine dissociation inhibitor (GDI) protein, an isoprene binding domain of the guanine dissociation inhibitor, a GAP protein, an $AIF_4—$, a guanylyl 5-thiophosphate, a Y-27632, a C3 transferase, a *Clostridium difficile* toxin A, a *Clostridium difficile* toxin B, a *Clostridium. sordellii* lethal toxin LT, a *Escherichia coli* cytotoxic necrotizing factor 1 (CNF1), a *Escherichia coli* cytotoxic necrotizing factor 2 (CNF2), a *Bordetella bronchiseptica* dermonecrotizing toxin (DNT) or mixtures thereof.

In some embodiments, the use of a lysosome-endosome fusion inhibitor is effective to increase the half-life of a toxin (e.g., botulinum toxin) by about more than 10%. In some embodiments, the use of a lysosome-endosome fusion inhibitor is effective to increase the half-life of a toxin (e.g., botulinum toxin) by about more than 25%. In some embodiments, the use of a lysosome-endosome fusion inhibitor is effective to increase the half-life of a toxin (e.g., botulinum toxin) by about more than 50%. In some embodiments, the use of a lysosome-endosome fusion inhibitor is effective to increase the half-life of a toxin (e.g., botulinum toxin) by about more than 100%.

In some embodiments, the present invention provides a method for decreasing (i.e., modulating) the half-life of the toxin in a mammal. In some embodiments, the method of decreasing the half-life comprises co-administering the mammal with the toxin and a lysosome-endosome fusion facilitator.

In some embodiments, the lysosome-endosome facilitator comprises a GTPase activator, a type III secreted toxin, or a mixture thereof. In some embodiments, the GTPase activator comprises a GEF protein, a GEF protein mimic or a mixture thereof. In some embodiments, a type III secreted toxin is a *Salmonella typhimurium* SopE, a *Salmonella* SptP, a *Yersinia pseudotubercolosis* YopE, a *Yersinia* YopT or a *Pseudomonas aeruginosa* ExoS.

In some embodiments, the use of a lysosome-endosome fusion facilitator is effective to decrease the half-life of a toxin (e.g., botulinum toxin) by about more than 10%. In some embodiments, the use of a lysosome-endosome fusion facilitator is effective to decrease the half-life of a toxin (e.g., botulinum toxin) by about more than 25%. In some embodiments, the use of a lysosome-endosome fusion facilitator is effective to decrease the half-life of a toxin (e.g., botulinum toxin) by about more than 50%. In some embodiments, the use of a lysosome-endosome fusion facilitator is effective to decrease the half-life of a toxin (e.g., botulinum toxin) by about more than 100%.

The present invention also features a toxin, e.g., a botulinum toxin, fused with a fusion facilitator or fusion inhibitor. The fusion may be carried out by conventional techniques known in the art.

The present invention also provides for a method of treating a biological disorder in a patient. In some embodiments, the method comprises co-administering a botulinum toxin and a lysosome-endosome fusion inhibitor to a patient in need thereof. Non-limiting examples of biological disorder include a neuromuscular disorder, an autonomic disorder and pain. The routes of administration include, without limitation, transdermal, peritoneal, subcutaneous, intramuscular, intravenous and intrarectal.

In some embodiments, the method of treating a neuromuscular disorder comprises locally co-administering a toxin and a lysosome-endosome fusion inhibitor to a group of muscles.

In some embodiments, the method of treating an autonomic disorder comprises locally administering a toxin and a lysosome-endosome fusion inhibitor to a gland.

In some embodiments, the method of treating pain comprises locally co-administering a toxin and a lysosome-endosome fusion inhibitor to a site of pain. In some embodiments, the method of treating pain comprises co-administering a toxin and a lysosome-endosome fusion inhibitor to a spinal cord.

The present invention also provides methods for treating toxin, e.g., botulinum toxin, intoxication in a mammal. In some embodiments, the method comprises administering a lysosome-endosome fusion facilitator to the mammal in need thereof, thereby treating botulinum intoxication.

The doses of the toxin (e.g., botulinum toxin) and/or lysosome-endosome fusion modulator to be administered depend on many factors. One of ordinary skill will be able to readily determine the specific dose for each specific compound.

Furthermore, the amount of the toxin and/or lysosome-endosome fusion modulator administered can vary widely according to the particular disorder being treated, its severity and other various patient variables including size, weight, age, and responsiveness to therapy. Such determinations are routine to one of ordinary skill in the art (see for example, Harrison's Principles of Internal Medicine (1998), edited by Anthony Fauci et al., 14th edition, published by McGraw Hill).

The toxins and/or lysosome-endosome fusion modulators of the invention may be admixed, encapsulated, conjugated or otherwise associated with other molecules or mixtures of compounds as, for example, liposomes, formulations (oral, rectal, topical, etc.) for assisting in uptake, distribution and/or absorption.

Pharmaceutical formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the compounds of the invention are in admixture with a topical delivery agent such as lipids, liposomes, fatty acids, fatty acid esters, steroids, chelating agents and surfactants. Preferred lipids and liposomes (Chariot™ reagent) include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Compounds of the invention may be encapsulated within liposomes or may form complexes thereto, in particular to cationic liposomes. Alternatively, compounds may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which compounds of the invention are administered in conjunction with one or more penetration enhancers surfactants and chelators. Preferred surfactants include fatty acids and/or esters or salts thereof, bile acids and/or salts thereof. Preferred bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydrofusidate and sodium glycodihydrofusidate. Preferred fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Compounds of the invention may be delivered orally, in granular form including sprayed dried particles, or complexed to form micro or nanoparticles. Compound complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylamino-methylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG).

Formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compounds of the present invention include, but are not limited to, solutions, emulsions, and liposome-containing formulations. These compounds may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compounds, e.g., toxins and/or lysosome-endosome fusion modulator, of the present invention may be formulated into any of many possible dosage forms such as, but not limited to, tablets, capsules, gel capsules, liquid syrups, soft gels, suppositories, and enemas. The compounds of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In some embodiments of the present invention the pharmaceutical compounds may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compounds and formulations is generally known to those skilled in the pharmaceutical and formulation arts and may be applied to the formulation of the compounds of the present invention.

The following non-limiting examples provide those of ordinary skill in the art with exemplary suitable methods for practicing the present invention, and are not intended to limit the scope of the invention.

Example 1

Treatment of Pain Associated with Muscle Disorder

A female patient is diagnosed as having temporomandibular joint (TMJ) dysfunction with subluxation of the joint and is treated with surgical orthoplasty meniscusectomy and condyle resection. However, she continues to have difficulty with opening and closing her jaw after the surgical procedures. The jaw continues to exhibit considerable pain and immobility after these surgical procedures. She is diagnosed as having post-surgical myofascial pain syndrome and is injected with 7 U/kg of botulinum toxin and a therapeutic amount of ATPase associated with cellular activities (AAA) type inhibitor into the masseter and temporalis muscles.

Several days after the injections she notes substantial improvement in her pain and reports that her jaw feels looser. This gradually improves over a 2 to 3 week period in which she notes increased ability to open the jaw and diminishing pain. The improved condition persists for more than 27 months after the original injection of the neurotoxin and the ATPase inhibitor.

Example 2

Treatment of Excessive Sweating

A 65 year old patient with excessive unilateral sweating is treated by administering 0.05 U/kg to about 2 U/kg of a botulinum toxin and a therapeutic amount of an ATPase inhibitor. The administration is to the gland nerve plexus, ganglion, spinal cord or central nervous system. The specific site of administration is to be determined by the physician's knowledge of the anatomy and physiology of the target glands and secretary cells. The cessation of excessive sweating after the modified neurotoxin treatment is more than 27 months.

Example 3

Peripheral Administration of a Modified Neurotoxin to Treat Nasopharyngeal Tumor Pain These tumors, most often squamous cell carcinomas, are usually in the fossa of Rosenmuller and may invade the base of the skull. Pain in the face is common. It is constant, dull-aching in nature.

A 35 year old patient presents a nasopharyngeal tumor type pain. Pain is found at the lower left cheek. The patient is treated by a bolus injection of between about 0.05 U/kg to about 2 U/kg of a botulinum toxin and a GTPase inhibitor intramuscularly to the cheek. The particular dose as well as the frequency of administrations depends upon a variety of factors within the skill of the treating physician, as previously set forth. Within 1–7 days after modified neurotoxin administration the patient's pain is substantially alleviated. The duration of the pain alleviation is more than 27 months.

Example 4

Accidental Overdose in the Treatment of Postherpetic Neuralgia-use of Lysosome-Endosome Fusion Facilitator as an Antidote In an exemplary scenario, a 76 year old man presents a postherpetic type pain. The pain is localized to the abdomen region. The patient is treated by a bolus injection of between about 0.05 U/kg to about 2 U/kg of a BOTOX® intradermally to the abdomen. The treating physician accidentally administers an excessive amount of BOTOX®. Upon realizing the error, the physician administers to the same area a therapeutically effective dose of a lysosome-endosome fusion facilitator. The particular dose as well as the frequency of administrations the lysosome-endosome fusion facilitator depend upon a variety of factors within the skill of the treating physician. Within 1 day after BOTOX® and corrective lysosome-endosome fusion facilitator administration, the patient's pain is substantially alleviated.

Various articles and patents have been cited here. The disclosures of these references are incorporated in their entirety herein by reference herein.

While this invention has been described with respect to various specific examples and embodiments, it is to be understood that the invention is not limited thereto and that it can be variously practiced with the scope of the following claims.

What is claimed is:

1. A method of treating a neuromuscular disorder in a patient, the method comprising locally co-administering a toxin and a lysosome-endosome fusion inhibitor to a group of muscles of the patient in need thereof.

2. A method of treating an autonomic disorder in a patient, the method comprising locally administering a toxin and a lysosome-endosome fusion inhibitor to a gland of the patient in need thereof.

3. A method of treating pain in a patient, the method comprising locally co-administering a toxin and a lysosome-endosome fusion inhibitor to a site of pain of the patient in need thereof.

4. A method of treating pain in a patient, the method comprising co-administering a toxin and a lysosome-endosome fusion inhibitor to a spinal cord of the patient in need thereof.

* * * * *